United States Patent [19]

Fukuto et al.

[11] 4,108,991

[45] Aug. 22, 1978

[54] N-AMINOSULFENYL DERIVATIVES OF ALDICARB

[75] Inventors: Tetsuo Roy Fukuto, Riverside, Calif.; Allan Lindsay Black, Balmain, Australia

[73] Assignee: The Regents of the University of California, Berkeley, Calif.

[21] Appl. No.: 747,752

[22] Filed: Dec. 6, 1976

[51] Int. Cl.$^2$ ..................... C07C 131/00; A01N 9/12
[52] U.S. Cl. ................................. 424/248.5; 424/244; 424/250; 424/267; 424/274; 424/327; 260/239 BF; 260/293.85; 260/326.42; 260/566 AC; 544/158; 544/383
[58] Field of Search .............. 260/566 AC, 239 BF, 260/293.85, 326.42, 250 B, 250 BN; 424/244, 250, 267, 274, 248.5; 544/158

[56] References Cited

PUBLICATIONS

Fukuto et al., "Environmental Quality and Safety", supplement vol. III, Pesticides, Lectures held at the IUPAC Third International Congress of Pesticide Chemistry, Helsinki, 3–9 Jul. 1974, published 12–75, pp. 394–400.

*Primary Examiner*—Gerald A. Schwartz
*Attorney, Agent, or Firm*—Robert L. Andersen; H. Robinson Ertelt

[57] ABSTRACT

New pesticidal N-aminosulfenyl derivatives of aldicarb and their use to control insects and acarids are described.

10 Claims, No Drawings

N-AMINOSULFENYL DERIVATIVES OF ALDICARB

The compounds of this invention are N-aminosulfenyl derivatives of aldicarb. Aldicarb, the common name of 2-methyl-2-(methylthio)propanal O-(methylcarbamoyl)oxime, is a known insecticide and is described in U.S. Pat. No. 3,217,037 issued Nov. 9, 1965.

The aminosulfenyl derivatives of aldicarb have not previously been described. They are highly effective agents for the control of mites and a variety of insect pests, including those attacking crops and animals as well as those which are disease vectors. The toxicity of aldicarb has been a serious problem. Unexpectedly, the aminosulfenyl derivatives of aldicarb show substantially comparable levels of insecticidal and acaricidal activity, but with substantially decreased mammalian toxicity.

The new pesticidal N-aminosulfenyl derivatives of aldicarb which comprise this invention have the formula

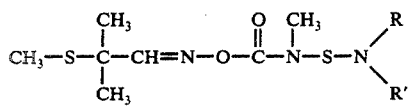

wherein R and R' are each independently straight or branched chain alkyl of 1 to 6 carbon atoms, phenyl, or phenylalkyl in which the alkyl portion is straight or branched chain of 1 to 3 carbon atoms, or R and R' taken together with the nitrogen form a piperidine, morpholine, pyrollidine, piperazine, or hexahydroazepine heterocyclic ring.

In the preferred embodiments, the foregoing is subject to the proviso that when one of R and R' is either phenyl or phenylalkyl, the other is alkyl. Thus, in one embodiment R and R' are each independently selected straight or branched chain alkyl groups having 1 to 6 carbon atoms, preferably 1 to 4 carbon atoms. In a second embodiment, one of R and R' is a straight or branched alkyl having 1 to 6 carbon atoms, preferably 1 to 4 carbon atoms, and the other is phenyl or phenylalkyl in which the alkyl portion is a straight or branched chain of 1 to 3 carbon atoms, preferably 1 to 2 carbon atoms. In a third embodiment, wherein R and R' combine to form a heterocyclic ring, it is preferred that R and R' taken together with the nitrogen form a morpholine or piperidine ring.

The compounds of the present invention may be prepared by the reaction of a sulfenyl halide of the formula X—S—NRR', wherein X is halogen, preferably Br or Cl, with aldicarb in the presence of at least enough base to neutralize the HX formed. The reaction is conveniently carried out at about room temperature, for example 20°–25° C., but may be carried out at about 0°–80° C.

The preparation and pesticidal properties of the compounds of this invention are illustrated in the following specific examples. Unless otherwise specified, all temperatures are in degrees centigrade, and concentration of liquid volume was carried out under the reduced pressure produced by a water aspirator.

EXAMPLE I

Synthesis of 2-methyl-2-(methylthio)propanol O-[(N-benzyl-N-methylaminosulfenyl)(methyl)carbamoyl]oxime

A. Preparation of N-benzyl-N-methylaminosulfenyl chloride

Benzylmethylamine (121.0 g) was added dropwise with stirring to a cold (0°–5°) solution of sulfur monochloride (33.7 g) in carbon tetrachloride (550 ml). The rate of addition was controlled to maintain the temperature in the range of 0°–5°. The reaction mixture was stirred at 0°–5° for a half hour, then at room temperature for an additional half hour. The reaction mixture was filtered to remove the benzylmethylamine hydrochloride precipitate, and the filter cake was washed three times with 100 ml portions of carbon tetrachloride. The filtrate and washings were combined, cooled to 0°, and chlorine (20.0 g) was bubbled into the stirred solution. The mixture was stirred for an additional 15 minutes at 0°, then for 45 minutes at room temperature. The reaction mixture was filtered, and the filtrate concentrated to give N-benzyl-N-methylaminosulfenyl chloride (66.9 g), which was used without further purification.

B. Reaction of N-benzyl-N-methylaminosulfenyl chloride with aldicarb

Into a 100 ml, three-necked, round bottom flask, fitted with a condenser protected by a drying tube, a thermometer, a dropping funnel, and a magnetic stirrer, was placed 22.0 g of N-benzyl-N-methylaminosulfenyl chloride. The flask with its contents were cooled to approximately 5° at which temperature 9.5 g of 2-methyl-2-(methylthio)propanol O-(methylcarbamoyl)oxime (aldicarb) dissolved in 50 ml of pyridine was added dropwise during 20 minutes. The reaction mixture was stirred at 5° for 1 hour, at room temperature for 17 hours, then filtered. The filtrate was poured into 250 ml of water and extracted three times with 100 ml of hexane. The combined hexane extracts were washed three times with 100 ml portions of 10% hydrochloric acid, twice with 100 ml saturated sodium bicarbonate solution, and once with 100 ml water. After drying over anhydrous sodium sulfate, the hexane was evaporated leaving 13.1 g of orange liquid. The orange liquid, dissolved in hexane, was placed on a column of 75 g of silica gel and eluted first with hexane (840 ml), then with toluene:hexane mixtures as follows: (1) 10:90 (200 ml), (2) 25:75 (240 ml), (3) 40:60 (520 ml), (4) 75:25 (400 ml), (5) 85:15 (400 ml), and then with toluene. Ir monitoring of elution revealed the desired product was eluted in the 75:25 and 85:15 fractions of toluene:hexane, and in the first 120 ml of toluene. These fractions were combined and solvent removed by heating on a steam bath under a nitrogen stream, yielding 2.2 g of the desired 2-methyl-2-(methylthio)propanol O-[(N-benzyl-N-methylaminosulfenyl)(methyl)-carbamoyl]oxime.

The ir spectra and nmr spectrum were consistent with the assigned structure.

Analysis calc'd for: $C_{15}H_{23}N_3O_2S_2$: C 52.76; H 6.79; N 12.30; O 9.37; S 18.78. Found: C 53.20; H 6.65; N 12.40; O —; S —.

EXAMPLE II

Synthesis of 2-methyl-2-(methylthio)propanol O-[(N-methyl-N-morpholinosulfenyl)carbamoyl]oxime

A. Preparation of morpholinosulfenyl chloride

A solution of morpholine (21.79 g) and triethylamine (25.25 g) in diethyl ether (300 ml) was added dropwise with stirring to a cold (0°–5°) solution of sulfur dichloride (51.48 g) in diethyl ether (300 ml). The rate of addition was controlled to maintain the temperature in the range of 0°–5°. The reaction mixture was stirred at 0°–5° for a half hour, then at room temperature for an additional half hour. The reaction mixture was filtered to remove the triethylamine hydrochloride precipitate, and the filtrate concentrated under reduced pressure. Vacuum distillation of the residue gave morpholinosulfenyl chloride (20.80 g), b.p. 62°–63°/0.11 mm Hg.

B. Reaction of morpholinosulfenyl chloride with aldicarb

Into a 100 ml, three-necked, round bottom flask, fitted with a condenser protected by a drying tube, a thermometer, a dropping funnel, and a magnetic stirrer, was placed 8.4 g of morpholinosulfenyl chloride. The flask and its contents were cooled to approximately 5° at which temperature 7.8 g of 2-methyl-2-(methylthio)-propanol O-(methylcarbamoyl)oxime (aldicarb) dissolved in 50 ml of pyridine was added dropwise during a 0.5 hour period. The reaction mixture was stirred at room temperature for approximately 20 hours and then filtered. To the filtrate was added 200 ml of water. After stirring for 15 minutes, the filtrate was extracted three times with 100 ml of hexane and then three times with 100 ml of toluene. The combined hexane extracts were washed three times with 100 ml of 10% hydrochloric acid, twice with 100 ml of saturated sodium bicarbonate solution, and once with 100 ml of water. After being dried over anhydrous sodium sulfate, the hexane was evaporated leaving a yellow oil weighing 4.2 g. The same washing procedure was used on the combined toluene extracts. A brown solid weighing 2.9 g remained after the toluene was removed, and was identified as starting material (aldicarb) by ir spectrum. The yellow oil from the hexane extract was solidified by a pentane wash, yielding 2.4 g of slightly yellow 2-methyl-2-(methylthio)propanol O-[N-methyl-N-morpholinosulfenyl)carbamoyl]-oxime, mp 69°–72°. The nmr spectrum was consistent with the assigned structure.

Analysis calc'd for $C_{11}H_{21}N_3O_3S_2$: C 42.97; H 6.89; N 13.67; O 15.61; S 20.86. Found: C 42.69; H 6.68; N 13.39; O —; S —.

EXAMPLE III

Synthesis of 2-methyl-2-(methylthio)propanal O-[(dibutylaminosulfenyl)(methyl)carbamoyl]oxime

A. Preparation of di-n-butylaminosulfenyl chloride

Sulfur monochloride (16.9 g) was added dropwise with stirring to a cold (0°–5°) solution of di-n-butylamine (64.5 g) in hexane (500 ml). The rate of addition was controlled to maintain the temperature in the range of 0°–5°. The reaction mixture was stirred at 0°–5° for an additional half hour, then at room temperature for 1 hour. The mixture was filtered to remove the di-n-butylamine hydrochloride precipitate, and the filtrate was concentrated to give a residue (38.4 g), which was dissolved in carbon tetrachloride (400 ml). The carbon tetrachloride solution was cooled to 0°–5°, and chlorine (9.7 g) was bubbled into the solution with stirring. The reaction mixture was stirred at 0°–5° for a half hour, then at room temperature for an additional half hour, filtered, and the filtrate concentrated to give, after vacuum distillation, di-n-butylaminosulfenyl chloride (21.9 g), b.p. 66°–68°/0.18 mm Hg.

B. Reaction of di-n-butylaminosulfenyl chloride with aldicarb

Into a flask was placed 14.7 g of di-n-butylaminosulfenyl chloride. The flask and its contents were cooled to 5° and 9.5 g of 2-methyl-2-(methylthio)propanal O-(methylcarbamoyl(oxime (aldicarb) dissolved in 50 ml pyridine was added dropwise. The reaction mixture was stirred for 1 hour at 5° and then 16 hours at room temperature. The resulting slurry was filtered at room temperature and the filtrate was poured into 200 ml of water. The filtrate was extracted with 3 portions (100 ml each) of hexane. The combined hexane extracts were washed three times with 100 ml portions of 10% hydrochloric acid, twice with saturated sodium bicarbonate solution, and once with water (100 ml) and dried over anhydrous sodium sulfate. The solvent was removed on a rotary evaporator leaving an orange oil weighing 5.1 g. The orange oil was placed on a column of 20 g of silica gel and hexane. Elution was carried out with hexane (360 ml), then the following toluene:hexane mixtures: (1) 10:90 (80 ml), (2) 20:80 (40 ml), (3) 40:60 (40 ml), (4) 60:40 (60 ml), (5) 80:20 (100 ml), followed by toluene (520 ml), and then by the following chloroform:toluene mixtures: (1) 20:80 (80 ml), (2) 50:50 (80 ml). Ir monitoring of fractions revealed the desired product was present in fractions eluted with 40:60, 60:40, 80:20, toluene:hexane, toluene, and the toluene:chloroform fractions. These fractions were transferred with chloroform and the solvent evaporated by heating on a steam bath under a nitrogen stream to yield 0.85 g of the desired 2-methyl-2-(methylthio)propanal O-[(dibutylaminosulfenyl)(methyl)carbamoyl]-oxime. The ir spectrum and nmr spectrum were consistent with the assigned structure.

Analysis calc'd for $C_{15}H_{31}N_3S_2O_2$: C 51.54; H 8.94; N 12.02; S 18.35; O 9.15. Found: C 50.86; H 9.36; N 12.30; S —; O —; C 50.73; H 9.23; N 12.31; S —; O —.

EXAMPLE IV

2-Methyl-2-(methylthio)propanal O-[(dimethylaminosulfenyl)-(methyl)carbamoyl]oxime is prepared in the same manner as the compound of Example III except that dimethylaminosulfenyl chloride is used instead of dibutylaminosulfenyl chloride.

EXAMPLE V

Toxicity to Rats

Method A: Young female albino rats, derived from Sprague-Dawley stock and weighing between 175 and 200 g, were used. An initial screening was conducted to determine the general level of toxicity of the test compounds and to establish the dosing range to be used with each compound. The test materials were suspended in corn oil and administered directly into the stomachs of the rats, using a hypodermic syringe equipped with a ball-tipped intubating needle. A range of dosing levels was employed utilizing two rats at each level. After oral administration of the test material, the rats were observed for 14 days after which time the acute oral median lethal dose ($LD_{50}$) was determined. This method was used to determine the toxicity to rats of the compounds of Examples I, II, and III and aldicarb. Results are presented in Table 1. The $LD_{50}$ value of the compound of Example II was 2.4 times as high as that of aldicarb. For the compounds of Examples I and III the $LD_{50}$ values were respectively 19 and 25 times greater than that of aldicarb. This demonstrates the substantially reduced mammalian toxicity of the aminosulfenyl derivatives.

TABLE 1

| Compound of Example | TOXICITY TO RATS | |
|---|---|---|
| | $LD_{50}$(mg/kg) | Enhancement $LD_{50}$Derivative/ $LD_{50}$Aldicarb |
| I | 9.4 | 19 |
| II | 1.2 | 2.4 |
| III | 12.5 | 25 |
| Aldicarb | 0.5 | — |

EXAMPLE VI

Toxicity to Insects and Mites

Initial Contact Activity: One half gram of test compound was dissolved in 40 ml of acetone and this solution was dispersed in 360 ml of water containing one drop of isooctylphenyl polyethoxyethanol. Aliquots of this solution, which corresponds to 1250 ppm of active ingredient, were diluted with an appropriate amount of water to provide solutions containing various concentrations of active ingredient. Test organisms and techniques were as follows: The activity against the Mexican bean beetle (*Epilachna varivestis* Muls.) and the southern armyworm (*Spodoptera eridania* [Cram.]) was evaluated by dipping the leaves of pinto bean plants into the test solution and infesting the leaves with the appropriate immature-form insects when the foliage had dried; the activity against the pea aphid (*Acyrthosiphon pisum* [Harris]) was evaluated on broad bean plants whose leaves were dipped before infestation with adult aphids; the activity against two-sotted spider mites (*Tetranychus urticae* Koch) was evaluated on pinto bean plants whose leaves were dipped after infestation with adult mites; the activity against the milkweed bug (*Oncopeltus fasciatus* [Dallas]), and the plum curculio (*Conotrachelus nenuphar* [Herbst]) was evaluated by spraying the test solutions into glass dishes or jars containing the adult insects; the activity against the confused flour beetle (*Tribolium confusum* duVal) was evaluated by introducing the insects into glass dishes which had been previously sprayed with test solution and allowed to to dry. All organisms in the test were maintained in a holding room at 80° F and 50% relative humidity for an exposure period of 48 hours. At the end of this time, the dead and living insects or mites were counted, and the percent kill was calculated. Results of these tests are summarized in Table 2. In general, the compounds of the present invention exhibit an initial toxicity to insects and mites which is in the same range as that of aldicarb.

Residual Contact Activity: The residual contact activity of the compounds was determined on the same organisms using the techniques described above, except that in each case the treated surface was allowed to dry and was exposed to normal light and air for seven days before introduction of the mites or insects. Results of these tests are summarized in Table 3. In general, the compounds exhibit a residual activity which is substantially the same as, or slightly better than, that of aldicarb.

Systemic Activity: Systemic activity was measured using a soil-watering technique. Test organisms were Mexican bean beetle, southern armyworm, pea aphid, and mites on plants as described above in this Example. With appropriate precautions to avoid contact of the solution with the test plant surfaces, 25 ml of a test solution, prepared as above to contain the desired amount of active ingredient, were poured evenly over the surface of the soil in which the plant was growing. The treated plants were maintained under normal growing conditions for three days to permit translocation of the toxicant, after which the leaves were infested. Two days after infestation, counts of living and dead insects were made. These results are summarized in Table 4. In general, in this test of systemic activity, the compounds of the present invention are slightly less effective than aldicarb, except for the compound of Example 4 which appears to be substantially the same as aldicarb.

TABLE 2

| Compound | Conc. (PPM) | INITIAL INSECTICIDAL ACTIVITY Percent Kill | | | | | | | |
|---|---|---|---|---|---|---|---|---|---|
| | | BB* | PA* | AW* | SM* | MWB* | PC* | GW* | FB* |
| Example I | 1250 | 100 | 100 | 33 | 100 | 100 | 45 | 100 | 2.5 |
| | 625 | 100 | — | 25 | — | — | — | — | — |
| | 312 | 94 | — | 24 | — | — | — | 100 | 5 |
| | 156 | 82 | 100 | 0 | 100 | 100 | 0 | 100 | 5 |
| | 39 | — | 62 | — | 98 | 80 | 0 | — | — |
| | 10 | — | 20 | — | 96 | 5 | 10 | — | — |
| Example II | 1250 | 100 | 100 | 100 | 100 | 100 | 100 | 100 | 80 |
| | 625 | 100 | — | 70 | — | — | — | — | — |
| | 312 | 100 | — | 0 | — | — | — | 100 | 51 |
| | 156 | 100 | 100 | 0 | 100 | 100 | 47 | 100 | 5 |
| | 39 | — | 100 | — | 100 | 100 | 5 | — | — |
| | 10 | — | 78 | — | 100 | 25 | 0 | — | — |
| Example III | 1250 | 100 | 100 | 20 | 100 | 100 | 55 | 100 | 70 |
| | 625 | 95 | — | 0 | — | — | — | — | — |
| | 312 | 63 | — | 0 | — | — | — | 100 | 7.5 |
| | 156 | 40 | 100 | 0 | 100 | 100 | 0 | 100 | 0 |
| | 39 | — | 19 | — | 89 | 16 | 5 | — | — |
| | 10 | — | 53 | — | 98 | 5 | 0 | — | — |
| Aldicarb | 1250 | 100 | 100 | 87 | 95 | 100 | 100 | 100 | 90 |
| | 625 | 100 | — | 15 | — | — | — | — | — |
| | 312 | 95 | — | 0 | — | — | — | 100 | 10 |
| | 156 | 91 | 100 | 23 | 100 | 100 | 100 | 97.5 | 5 |
| | 39 | — | 85 | — | 97 | 100 | 35 | — | — |
| | 10 | — | 33 | — | 100 | 70 | 10 | — | — |
| Untreated check | | 0 | 0 | 0 | 0.9 | 0 | 0 | 0 | 0 |
| Example IV | 1250 | 100 | 100 | 12 | 100 | 100 | | 100 | |
| | 625 | — | — | 0 | — | — | | — | |

TABLE 2-continued
INITIAL INSECTICIDAL ACTIVITY

| Compound | Conc. (PPM) | BB* | PA* | AW* | SM* | MWB* | PC* | GW* | FB* |
|---|---|---|---|---|---|---|---|---|---|
| | 312 | — | — | 0 | — | — | | — | |
| | 156 | 39 | 95 | 0 | 0 | — | | 50 | |
| | 39 | 6 | 5 | — | 100 | — | | 5 | |
| | 20 | 5 | 0 | — | 83 | 43 | | 0 | |
| | 10 | — | — | — | 36 | 26 | | — | |
| | 5 | — | — | — | 17 | 20 | | — | |
| Aldicarb | 1250 | — | — | 0 | 100 | — | | — | |
| | 625 | — | — | 12 | — | — | | — | |
| | 312 | — | — | 0 | — | — | | — | |
| | 156 | 89 | 100 | — | — | — | | 100 | |
| | 39 | 40 | 60 | — | 100 | — | | 40 | |
| | 20 | 0 | 35 | — | 100 | 95 | | 20 | |
| | 10 | — | — | — | 88 | 55 | | — | |
| | 5 | — | — | — | 21 | 30 | | — | |
| Untreated check | | 0 | 0 | — | 0 | 0 | | 0 | |

*BB: Mexican bean beetle
AW: Southern armyworm
PA: Pea aphid
SM: Two-spotted spider mite
MWB: Milkweed bug
PC: Plum curculio
FB: Confused flour beetle
GW: Granary Weevil

TABLE 3
RESIDUAL (7-DAY) TOXICITY TO INSECTS AND MITES

| Compound | Conc. (PPM) | BB* | PA* | AW* | SM* | MWB* | PC* | GW* | FB* |
|---|---|---|---|---|---|---|---|---|---|
| Example I | 1250 | 89 | 100 | 91 | 99.5 | 100 | 20 | 100 | 2.6 |
| | 312 | 0 | 6.3 | 0 | 63 | 95 | 43 | 41 | 0 |
| | 156 | — | 0 | — | 3.2 | 90 | 23 | — | — |
| Example II | 1250 | 100 | 93 | 55 | 97 | 100 | 37 | 100 | 2.5 |
| | 312 | 88 | 0 | 64 | 93 | 100 | 5 | 20 | 0 |
| | 156 | — | 0 | — | 76 | 100 | 10 | — | — |
| Example III | 1250 | 92 | 0 | 0 | 100 | 100 | 5 | 17 | 0 |
| | 312 | 0 | 0 | 0 | 45 | 70 | 9.5 | 0 | 0 |
| | 156 | — | 0 | — | 18 | 20 | 5 | — | — |
| Aldicarb | 1250 | 100 | 100 | 86 | 98.6 | 100 | 0 | 0 | 0 |
| | 312 | 93 | 0 | 0 | 97 | 80 | 32 | 3.3 | 0 |
| | 156 | — | 0 | — | 91.5 | 15 | 4.8 | — | — |
| Untreated check | | 0 | 0 | 0 | 0 | 0 | 6.7 | 4.5 | 0 |
| Example IV | 1250 | 50 | 5 | 20 | 100 | 100 | 0 | | |
| | 625 | 40 | 5 | 0 | 0 | 100 | 0 | | |
| | 312 | 17 | 10 | — | — | 65 | — | | |
| | 156 | — | — | — | 52 | — | — | | |
| | 39 | — | — | — | 18 | — | — | | |
| Aldicarb | 1250 | — | — | 40 | — | 100 | 0 | | |
| | 625 | 47 | 10 | 0 | — | 100 | 0 | | |
| | 312 | 11 | 40 | — | — | 70 | — | | |
| | 156 | — | — | — | 90 | — | — | | |
| | 39 | — | — | — | 17 | — | — | | |
| Untreated check | | 0 | 0 | 0 | 0 | 0 | 0 | | |

*See Footnote Table 2

TABLE 4
SYSTEMIC TOXICITY TO INSECTS AND MITES

| Compound | Conc. (PPM) | BB* | PA* | AW* | SM* |
|---|---|---|---|---|---|
| Example I | 625 | — | — | 84 | — |
| | 312 | — | — | 50 | — |
| | 156 | 75 | — | — | — |
| | 39 | 0 | 100 | — | — |
| | 10 | — | 0 | — | 4.3 |
| | 5 | — | — | — | 2.3 |
| | 2.5 | — | — | — | 0.9 |
| Example II | 625 | — | — | 100 | — |
| | 312 | — | — | 100 | — |
| | 156 | 100 | — | — | — |
| | 39 | 58 | 100 | — | 69 |
| | 10 | — | 40 | — | 38 |
| | 5 | — | — | — | 1.4 |
| | 2.5 | — | — | — | — |
| Example III | 625 | — | — | 68 | — |
| | 312 | — | — | 0 | — |
| | 156 | 100 | — | — | — |
| | 39 | 20 | 64 | — | — |
| | 10 | — | 0 | — | 0.7 |
| | 5 | — | — | — | 0 |
| | 2.5 | — | — | — | 0.9 |
| Aldicarb | 625 | — | — | 100 | — |
| | 312 | — | — | 100 | — |
| | 156 | 100 | — | — | — |
| | 39 | 100 | 100 | — | — |
| | 10 | — | 90 | — | 100 |
| | 5 | — | — | — | 13 |
| | 2.5 | — | — | — | 4.6 |
| Untreated check | | 4.8 | 0 | 0 | 1.8 |
| Example IV | 312 | 100 | 100 | 100 | 100 |
| | 39 | 100 | — | 0 | 100 |
| | 10 | — | 100 | — | — |
| | 5 | — | 100 | — | 100 |
| Aldicarb | 321 | — | 100 | — | — |
| | 39 | 95 | — | 50 | 100 |
| | 10 | — | 100 | — | — |
| | 5 | — | 100 | — | 98 |
| Untreated check | | — | 0 | 0 | 19 |

*See Footnote Table 2

It is anticipated that, in the normal use of the compounds of the present invention as insecticides, the compounds will usually not be employed free from admixture or dilution, but will ordinarily be used in a suitably formulated state compatible with the method of application. The pesticidal aminosulfenyl derivatives of aldicarb may be formulated with the usual additives and extenders used in the preparation of pesticidal compositions. The toxicants of this invention, like most pesticidal agents, are incorporated with the adjuvants and carriers normally employed for facilitating the dispersion of active ingredients, recognizing the accepted fact that the formulation and mode of application of a toxicant may affect the activity of the material. The present compounds may be applied, for example, as a spray, dust, or granule, to the area in which pest control is desired, the choice of application varying of course with the type of pest and the environment. Thus, these aminosulfenyl derivatives of aldicarb may be formulated as granules of large particle size, as powdery dusts, as wettable powders, as emulsifiable concentrates, as solutions, and the like.

Dusts are admixtures of the active ingredients with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of active ingredient, 30.0 parts of bentonite clay, and 60.0 parts of talc.

The compounds of the present invention may be made into liquid concentrates by solution or emulsion in suitable liquids, and into solid concentrates by admixtures with talc, clays, and other known solid carriers used in the pesticide art. The concentrates are compositions containing about 5-50% toxicant, and 95-50% inert material which includes dispersing agents, emulsifying agents, and wetting agents. The concentrates are diluted for practical application, with water or other liquid for sprays or with additional solid carrier for use as dusts. Typical carriers for solid concentrates (also called wettable powders) include fuller's earth, kaolin clays, silicas, and other highly absorbent, readily wet inorganic diluents. A solid concentrate formulation useful herein contains 1.5 parts each of sodium lignosulfonate and sodium laurylsulfate as wetting agents, 25.0 parts active ingredient, and 72.0 parts of bentonite clay.

Useful liquid concentrates include the emulsifiable concentrates, which are homogeneous liquid or paste compositions readily dispersed in water or other dispersant, and may consist entirely of the toxicant with a liquid or solid emulsifying agent, or may also contain a liquid carrier such as xylene, heavy aromatic naphthas, isophorone and other nonvolatile organic solvents. For application, these concentrates are dispersed in water or other liquid carrier, and normally applied as a spray to the area to be treated.

Typical wetting, dispersing or emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1-15% by weight of the pesticidal composition.

Other useful formulations include simple solutions of the active ingredient in a solvent in which it is completely soluble at the desired concentration, such as acetone or other organic solvents. Granular formulations, wherein the toxicant is carried on relatively coarse particles, are of particular utility.

The concentration of the toxicant in the dilution generally used for application is normally in the range of about 2% to about 0.001%. Many variations of spraying and dusting compositions in the art may be used by substituting a compound of this invention into compositions known or apparent to the art.

Pesticidal compositions may be formulated and applied with other active ingredients, including insecticides, nematicides, acaricides, fungicides, plant growth regulators, fertilizers, etc. In applying the chemicals, it is obvious that an effective amount and concentration of the aminosulfenyl derivative of aldicarb should be employed.

It is apparent that many modifications may be made in the preparation, formulation, and application of the compounds of this invention, without departing from the spirit and scope of the invention and of the following claims.

We claim:

1. A compound of the formula

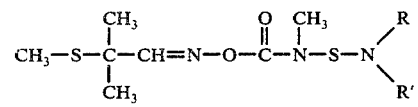

wherein R and R' are each independently straight or branched chain alkyl of 1 to 6 carbon atoms, phenyl or phenylalkyl wherein the alkyl portion is straight or branched chain of 1 to 3 carbon atoms, or R and R' taken together with the nitrogen form a piperidine, morpholine, pyrollidine, piperazine or hexahydroazepine ring.

2. A compound of claim 1 in which R and R' are each independently alkyl of 1 to 6 carbon atoms or one of R and R' is said alkyl and the other is phenyl or phenylalkyl wherein the alkyl portion is of 1 to 3 carbon atoms, or R and R' taken together with the nitrogen form a morpholine or piperidine ring.

3. The compound of claim 2 which is 2-methyl-2-(methylthio)propanal O-[(N-benzyl-N-methylaminosulfenyl)(methyl)carbamoyl]oxime.

4. The compound of claim 2 which is 2-methyl-2-(methylthio)propanal O-[(N-methyl-N-morpholinosulfenyl)-carbamoyl]oxime.

5. The compound of claim 2 which is 2-methyl-2-(methylthio)propanal O-[(dibutylaminosulfenyl)(methyl)-carbamoyl]oxime.

6. The compound of claim 2 which is 2-methyl-2-(methylthio)propanal O-[(dimethylaminosulfenyl)(methyl)-carbamoyl]oxime.

7. An insecticidal and acaricidal composition comprising an insecticidally effective amount of a compound of claim 1 in admixture with an agriculturally acceptable carrier.

8. An insecticidal and an acaricidal composition comprising an effective amount of a compound of claim 2 in admixture with an agriculturally acceptable carrier.

9. The method of controlling insects and acarids which comprises applying to the situs of infestation an insecticidally effective amount of the compound of claim 1.

10. The method of controlling insects and acarids which comprises applying to the situs of infestation an insecticidally effective amount of the compound of claim 2.

* * * * *

UNITED STATES PATENT AND TRADEMARK OFFICE
CERTIFICATE OF CORRECTION

PATENT NO. : 4,108,991
DATED : August 22, 1978
INVENTOR(S) : Tetsuo Roy Fukuto and Allan Lindsay Black It is certified that error appears in the above-identified patent and that said Letters Patent are hereby corrected as shown below:

```
Column 2, line 2, "propanol" should read --propanal--;
Column 2, line 38, "propanol" should read --propanal--;
Column 2, line 62, "propanol" should read --propanal--.
Column 3, line 2, "propanol" should read --propanal--;
Column 3, line 28, "propanol" should read --propanal--;
Column 3, line 47, "propanol" should read --propanal--;
Column 3, line 48, delete the hyphen before the word "oxime".
Column 4, line 15, "(oxime" should read --)oxime--; Column
4, line 41, delete the hyphen before the word "oxime";
Column 4, line 50, delete the hyphen before the word
"(methyl)".  Column 10, line 47, delete the hyphen before
the words "carbamoyl]oxime".
```

Signed and Sealed this

Fifteenth Day of January 1980

[SEAL]

Attest:

SIDNEY A. DIAMOND

Attesting Officer

Commissioner of Patents and Trademarks